United States Patent [19]

Zinninger et al.

[11] 4,404,016

[45] Sep. 13, 1983

[54] COMPOSITION AND METHOD FOR CONTROLLING GROWTH OF TOBACCO SUCKERS

[75] Inventors: Thomas C. Zinninger; Joseph Deli, both of Pittsburgh, Pa.

[73] Assignee: PPG Industries, Inc., Pittsburgh, Pa.

[21] Appl. No.: 306,055

[22] Filed: Sep. 28, 1981

[51] Int. Cl.³ ............... A01N 37/12; A01N 31/02; A01N 43/58

[52] U.S. Cl. ............... 71/78; 71/92; 71/111; 71/122

[58] Field of Search ............... 71/78, 111

[56] References Cited

U.S. PATENT DOCUMENTS

| | | | |
|---|---|---|---|
| 3,128,170 | 4/1964 | Plant | 71/111 |
| 3,253,904 | 5/1966 | Harrison | 71/111 |
| 3,326,664 | 6/1967 | Tso | 71/2.6 |
| 3,438,765 | 4/1969 | Tso et al. | 71/78 |
| 4,047,925 | 9/1977 | Barer | 71/78 |

FOREIGN PATENT DOCUMENTS 944570 12/1963 United Kingdom ........... 71/DIG. 1

OTHER PUBLICATIONS

Shell Int. Res., "Concentrated oil, etc.," (1980), CA 94, No. 78426d., (1981).
Pilmenshtein et al., "Freeze resistance, etc.," (1976), CA 91, No. 135,587w., (1979).

*Primary Examiner*—Glennon H. Hollrah
*Attorney, Agent, or Firm*—Edward J. Whitfield

[57] ABSTRACT

Sucker growth on tobacco plants is controlled by applying to the topped plants, after application of a contact sucker control agent or a contact and a systemic sucker control agent, a solution of alkyl N-(halophenyl)carbamate, e.g., CIPC, in alkylene glycol, e.g., ethylene glycol.

4 Claims, No Drawings

COMPOSITION AND METHOD FOR CONTROLLING GROWTH OF TOBACCO SUCKERS

FIELD OF THE INVENTION

This invention relates to a chemical composition and method of controlling, i.e., inhibiting, the growth of suckers on tobacco plants. Sucker growth on tobacco plants is typically controlled by one or more periodic applications of contact sucker control agent, e.g., saturated fatty alcohol, to the plant, after topping which treatment is usually followed by one or more periodic applications of systemic sucker control agent, e.g., maleic hydrazide. Although this mode of treatment provides satisfactory sucker control, the tobacco plants have been found to contain undesirably high residues of maleic hydrazide, which is a suspected carcinogen.

Alkyl N-(halophenyl)carbamates, e.g., isopropyl N-(3-chlorophenyl) carbamate, are known to provide satisfactory control of sucker growth; however, when applied to typical sucker controlling amounts, these materials ordinarily cause deformation, i.e., puckering, of the tobacco plant leaf.

DESCRIPTION OF THE INVENTION

This invention provides means for controlling, i.e., inhibiting, the growth of tobacco suckers, by applying to topped tobacco plants, that have been previously treated with contact sucker control agent, e.g., saturated fatty alcohol, a liquid composition comprising an alkylene glycol solution of alkyl N-(halophenyl)carbamate, e.g., isopropyl N-(3-chlorophenyl)carbamate. The quantity of alky N-(halophenyl)carbamate in the composition may vary over a wide range, for example, from about 1.0 percent by weight up to the maximum solubility of the carbamate in the alkylene glycol. For example, the solubility of isopropyl N-(3-chlorophenyl) carbamate (CIPC) in monoethylene glycol is about 0.156 gram per milliliter at ambient temperature. Typically the composition contains from about 8 to 14 percent by weight and preferably from about 12 to 14 percent by weight carbamate based on weight of alkylene glycol. Suitable alkylene glycols for use in accordance with this invention include ethylene glycol, propylene glycol, or mixtures of ethylene and propylene glycol.

The composition of this invention is typically applied to topped tobacco plants by forming an aqueous emulsion of the composition in the presence of a suitable wetting or emulsifying agent and spraying onto the upper parts of the topped tobacco plants. The rate of application of the composition of this invention will, of course, depend on several factors, such as, for example, the stage of plant growth, the density of plant growth, soil and climatic conditions, and the like. In general the rate of application is determined by the plant density, i.e., the number of plants per acre, which typically ranges from about 5,000 to 8,000 plants per acre. Typically sufficient composition of this invention is applied so as to provide from about 10 to about 200 milligrams and preferably from about 20 to 100 milligrams of carbamate compound per tobacco plant.

In a typical practice of this invention, the tobacco plants are topped when they reach the full-flower stage, any suckers are removed by hand, and commercial contact sucker control agent is applied in conventional fashion, e.g., by spraying an aqueous emulsion onto the plants. Commonly used contact sucker control agents are $C_6$ to $C_{18}$ saturated fatty alcohols, for example, n-hexanol, n-octanol, n-decanol, n-dodecanol, n-tetradecanol, n-hexadecanol or mixtures thereof. About 5 to 7 days after application of contact sucker control agent, the composition of this invention is applied as before described, which effectively inhibits further growth of suckers.

If extended sucker control through the harvest season is desired, a commercial contact sucker control agent is applied when about 50 percent of the plants have reached the button stage of flower development. About 5 to 7 days after application of contact sucker control agent the plants are topped and conventional systemic sucker control agent is applied. Maleic hydrazide is, as beforesaid, the most widely used systemic sucker control agent. About 7 to 10 days following application of systemic sucker control agent, the composition of this invention is applied in the manner described hereinabove, which effectively inhibits further growth of suckers.

The efficacy of a preferred composition of this invention in controlling sucker growth on tobacco plants is illustrated by the following Examples.

EXAMPLE I

A formulation was prepared containing 12.0 percent by weight of isopropyl N-(3-chlorophenyl)carbamate (CIPC), 80.5 weight percent of monoethylene glycol and 7.5 weight percent of "Atlas G-3300", a commercial emulsifying agent obtained from Imperial Chemicals Industry Ltd. The formulation had a specific gravity of 1.116 and contained 1.12 pounds per gallon (134 grams per liter) of isopropyl N-(3-chlorophenyl) carbamate.

EXAMPLE II

Tests were conducted under the auspices of the Regional Tobacco Growth Regulator Committee at various locations in the southeastern United States, under actual field conditions, to determine the relative sucker control effectiveness on flue-cured tobaccos of conventional chemical treatments and chemical treatments employing a formulation of this invention, i.e., the formulation prepared as described in Example I. More particularly, the following types of treatment were compared.

(a) FA/FA—This treatment involved sequential spraying of an aqueous emulsion of a commercial contact sucker control agent, namely, Off-Shoot T-85, a fatty alcohol formulation manufactured by Proctor & Gamble. In the first stage of the treatment, untopped tobacco plants, in the early to late bud stage of flower development, were sprayed with a 3 to 4 percent aqueous emulsion so as to apply from 0.8 to 1.2 milliliters of said undiluted formulation per tobacco plant. The plants were permitted to develop to the early to full flower stage when they were topped and sprayed a second time with a 3 to 4 percent aqueous emulsion of said formulation so as to again deposit from 0.8 to 1.2 milliliters of undiluted formulation on the upper portion of each topped plant.

(b) FA/KMH—This treatment involved spraying of 3 to 4 percent aqueous emulsion of the contact fatty alcohol sucker control formulation as described in paragraph (a) onto untopped plants in the early to late bud stage so as to deposit from 0.8 to 1.2 milliliters of undiluted formulation on each untopped plant. After the plants developed to the early to full flower stage, the plants were topped and treated by spraying a systemic sucker control agent, namely, a 3.2 to 4.8 percent aqueous emulsion of "Royal MH-30" (a commercially available formulation of maleic hydrazide potassium salt) so as to deposit about 170 milligrams of maleic hydrazide on the upper portion of each topped plant.

(c) FA/I—This treatment involved spraying of a 3 to 4 percent aqueous emulsion of the contact fatty alcohol sucker control formulation as described in paragraphs (a) and (b) onto untopped plants in the early to late bud stage so as to deposit from 0.8 to 1.2 milliliters of undiluted formulation on each untopped plant. After the plants developed to the early to full flower stages, the plants were topped and treated by spraying an about 5 percent aqueous emulsion of the formulation prepared as described in Example I onto their upper parts so as to deposit about 150 milligrams of isopropyl N-(3-chlorophenyl)carbamate on each plant.

(d) FA/0.5 KMH/I—The first two steps of this treatment were carried out as described in paragraph (c) except that one half the amount of maleic hydrazide, i.e., about 85 milligrams, was applied to each plant. From 5 to 7 days after application of the maleic hydrazide, the plants were sprayed with an about 5 percent aqueous emulsion of the formulation prepared as described in Example I, so as to deposit about 150 milligrams of isopropyl N-(3-chlorophenyl)carbamate on each plant.

(e) TNS—Each of the above-described modes of treatment was evaluated against a control plot in which the tobacco plants were topped but which was not treated with any sucker control chemical or chemicals.

The treated and untreated tobacco plants were evaluated for extent of sucker control, leaf yield per acre and perhaps, most importantly, the acre index which is the dollar value of the leaf expressed in dollars per acre. The following Table presents the comparative Acre Indices expressed in dollars per acre of the untreated and treated tobacco crops at various test sites.

| | ACRE INDEX, $/A | | | | |
|---|---|---|---|---|---|
| LOCATION | TNS | FA/FA | FA/KMH | FA/I | FA/0.5 KMH/I |
| A | 2702 | — | 2763 | 2870 | — |
| B | 2961 | — | 4009 | 4048 | — |
| C | 2705 | — | 4538 | 4883 | — |
| D | 2209 | — | 3575 | 3788 | — |
| E | 2186 | 3314 | 3310 | — | 3468 |
| F | 3221 | 3915 | 3916 | — | 4021 |
| G | 2497 | 3813 | 4430 | — | 4517 |

As shown by the foregoing, the treatments wherein a formulation of the invention was employed (FA/I and FA/0.5 KMH/I) in all instances resulted in a higher acre index than conventional treatments involving sequential treatment with fatty alcohol contact control agent (FA/FA) and sequential treatment with fatty alcohol contact control agent and maleic hydrazide systemic control agent (FA/KMH).

Although the invention has been described in considerable detail by the foregoing, it is to be understood that the invention be so limited, since many variations may be made therein by those skilled in the art without departing from the spirit and scope thereof, except as appears in the appended claims.

We claim:

1. In a method of controlling the growth of suckers on tobacco plants by sequentially treating the plants with one or more applications of $C_6$ to $C_{18}$ saturated fatty alcohol followed by one or more applications of maleic hydrazide wherein the improvement resides in applying to the topped plants, following application of either said fatty alcohol or maleic hydrazide, an effective sucker controlling amount of a solution of isopropyl N-(3 chlorophenyl) carbamate in alkylene glycol so as to provide from about 10 to about 200 milligrams of carbamate compound per tobacco plant.

2. The process of claim 1 wherein the alkylene glycol is selected from ethylene glycol, propylene glycol or mixtures thereof.

3. The process of claim 2 wherein the alkylene glycol is ethylene glycol.

4. The process of claim 1 wherein sufficient solution is applied so as to provide from about 20 to 100 milligrams of carbamate compound per tobacco plant.

* * * * *